United States Patent
Bushey et al.

(10) Patent No.: US 9,429,499 B2
(45) Date of Patent: Aug. 30, 2016

(54) METHODS, DEVICES, AND SYSTEMS FOR CONTROLLING THE RATE OF GAS DEPRESSURIZATION WITHIN A VIAL CONTAINING A GAS SAMPLE

(75) Inventors: Jared M Bushey, Newark, DE (US); Robert C Henderson, Avondale, PA (US); William H Wilson, Newark, DE (US)

(73) Assignee: Agilent Technologies, Inc., Loveland, CO (US)

( * ) Notice: Subject to any disclaimer, the term of this patent is extended or adjusted under 35 U.S.C. 154(b) by 1092 days.

(21) Appl. No.: 12/915,600

(22) Filed: Oct. 29, 2010

(65) Prior Publication Data
US 2012/0103063 A1    May 3, 2012

(51) Int. Cl.
*G01N 1/22* (2006.01)

(52) U.S. Cl.
CPC ..... *G01N 1/2226* (2013.01); *G01N 2001/2238* (2013.01); *Y10T 137/0379* (2015.04); *Y10T 137/7761* (2015.04)

(58) Field of Classification Search
CPC .................. G01N 1/2226; G01N 2001/2229; G01N 2001/2238
USPC .............................. 73/23.41, 864.63, 863.01
See application file for complete search history.

(56) References Cited

U.S. PATENT DOCUMENTS

| | | | |
|---|---|---|---|
| 4,373,549 A | 2/1983 | Nalepa et al. | 137/487.5 |
| 4,994,096 A | 2/1991 | Klein et al. | 95/15 |
| 5,108,466 A | 4/1992 | Klein et al. | 95/1 |
| 5,431,712 A | 7/1995 | Henderson et al. | 95/22 |
| 5,476,000 A | 12/1995 | Henderson et al. | 73/23.27 |
| 7,258,132 B2 | 8/2007 | Henderson et al. | 137/487.5 |
| 7,709,267 B2 * | 5/2010 | Tipler | G01N 1/2226 422/68.1 |
| 2006/0099718 A1 * | 5/2006 | Tipler | G01N 1/2226 436/174 |
| 2007/0184553 A1 * | 8/2007 | Hartlein | G01N 30/24 436/50 |

FOREIGN PATENT DOCUMENTS

| | | |
|---|---|---|
| CN | 201421467 Y | 3/2010 |
| JP | 2001523820 A | 11/2001 |
| JP | 2006523825 A | 10/2006 |

OTHER PUBLICATIONS

Office Action dated May 6, 2015 from the Chinese Intellectual Property Office for Application No. 201110304199.3.

(Continued)

*Primary Examiner* — Peter Macchiarolo
*Assistant Examiner* — Nathaniel Kolb

(57) ABSTRACT

The present invention relates to methods and systems for controlling depressurization of a vial containing a gas sample. The disclosed systems and methods are employed during sampling and/or analysis of the gas sample. One exemplary method for controlling depressurization of a vial containing a gas sample includes establishing fluid communication between a sample loop of a head space sampling device and the head space of the vial. A sample gas pressure is established within the head space of the vial. The sample loop is connected in fluid communication with a lower pressure environment through a ventilation pathway. A ventilation valve within the ventilation pathway is used to vent gas from the vial through the sample loop to the lower pressure environment at a predetermined rate. Devices and systems for depressurizing a vial containing a gas sample at a predetermined rate are also disclosed.

14 Claims, 10 Drawing Sheets

(56) References Cited

OTHER PUBLICATIONS

Office Action dated Jun. 23, 2015 from the Japanese Patent Office for Application No. 2011-208629.

Gudat et al., "Better precision, sensitivity, and higher sample throughput for the analysis of residual solvents in pharmaceuticals," Agilent Technologies, Inc., Publication No. 5989-6023EN (Feb. 15, 2007).

Chinese Office Action for Application No. 201110304199.3 mailed on Jan. 14, 2016, 3 pages.

* cited by examiner

| Analyte | Average Active Area* (pA*s) | Average Passive Area† (pA*s) | Passive Area as % of Active Area |
|---|---|---|---|
| EtOH | 357.98 | 251.93 | 70.38 |
| n-Propanol | 701.04 | 458.82 | 65.45 |

*Active experiment: Vial fill pressure = 15.00psig
Loop fill ramp rate = 20.00psig/min
Final loop pressure = 10.000psig
Final hold = 0.05min †Passive experiment: Vial fill pressure = 15.00psig
Loop fill ramp rate = 999.99psig/min
Final loop pressure = 0.000psig
Final hold = 0.00min

METHODS, DEVICES, AND SYSTEMS FOR CONTROLLING THE RATE OF GAS DEPRESSURIZATION WITHIN A VIAL CONTAINING A GAS SAMPLE

FIELD

This invention relates to systems and methods for controlling depressurization of a vial containing a gas sample. More particularly, this invention relates to systems and methods for depressurizing a vial containing a gas sample at a predetermined rate.

BACKGROUND

In conventional head space sample analysis, a liquid or solid sample is contained in a vial that is connected to a head space sampling device. The head space sampling device is used to sample the head space above the sample within the vial. Often, the sample is heated to produce a vapor that fills the head space. Prior to sampling of the head space, the vial is often pressurized with a gas that is provided to the vial in a controlled manner. For example, the vial typically can be pressurized by a gas until a selected pressure is reached. When desired pressure characteristics are present within the head space sampling device, the gas from the head space can be directed toward a head space analyzer.

Conventional head space sampling devices have a sample loop for receiving portions of a gas sample within the head space of a vial. These head space devices typically have a ventilation valve for venting gas from head space through the sample loop to the external pressure environment, thereby drawing portions of the gas sample from the vial to the sample loop. However, existing head space sampling devices cannot be programmed to precisely control the venting of the gas from the head space through the sample loop to the external pressure environment. Consequently, the amount of the gas sample that is transferred from the vial to the sample loop can vary significantly from sample to sample. Furthermore, sudden pressure changes resulting from venting of the gas from the head space through the sample loop to external pressure can shift any liquid/vapor equilibrium that was previously established within the system, thereby leading to inconsistent results. Additionally, venting of the gas from the head space to an undesirably low pressure can lead to insufficient pressures within the sample loop, and, therefore, insufficient gas sample concentrations within the sample loop.

Some conventional head space sampling devices have back pressure regulators for actively maintaining the pressure within the vial and the sample loop at a desired level. However, these devices require an additional gas source to actively regulate the vent pressure. Additionally, after the vial is pressurized, the opening of the ventilation valve can cause the pressure within the vial and the sample loop to rapidly decrease to the pressure set by the back pressure regulator. This rapid decrease in pressure makes it difficult to deliver consistent amounts of gas to the sample loop and the head space analyzer, leading to poor area repeatability during head space analysis.

Accordingly, there is a need in the pertinent art for automated and programmable systems and methods for depressurizing gas within a head space in a gradual, controlled manner to thereby maintain consistency in the gas sample concentrations that are sent to the gas analyzer. There is a further need in the pertinent art for automated and programmable systems and methods of depressurizing gas within a head space at a desired rate and to a desired pressure appropriate for any sample loop volume.

DETAILED DESCRIPTION OF THE FIGURES

These and other features of the preferred embodiments of the invention will become more apparent in the detailed description in which reference is made to the appended drawings wherein.

Figure 4A:
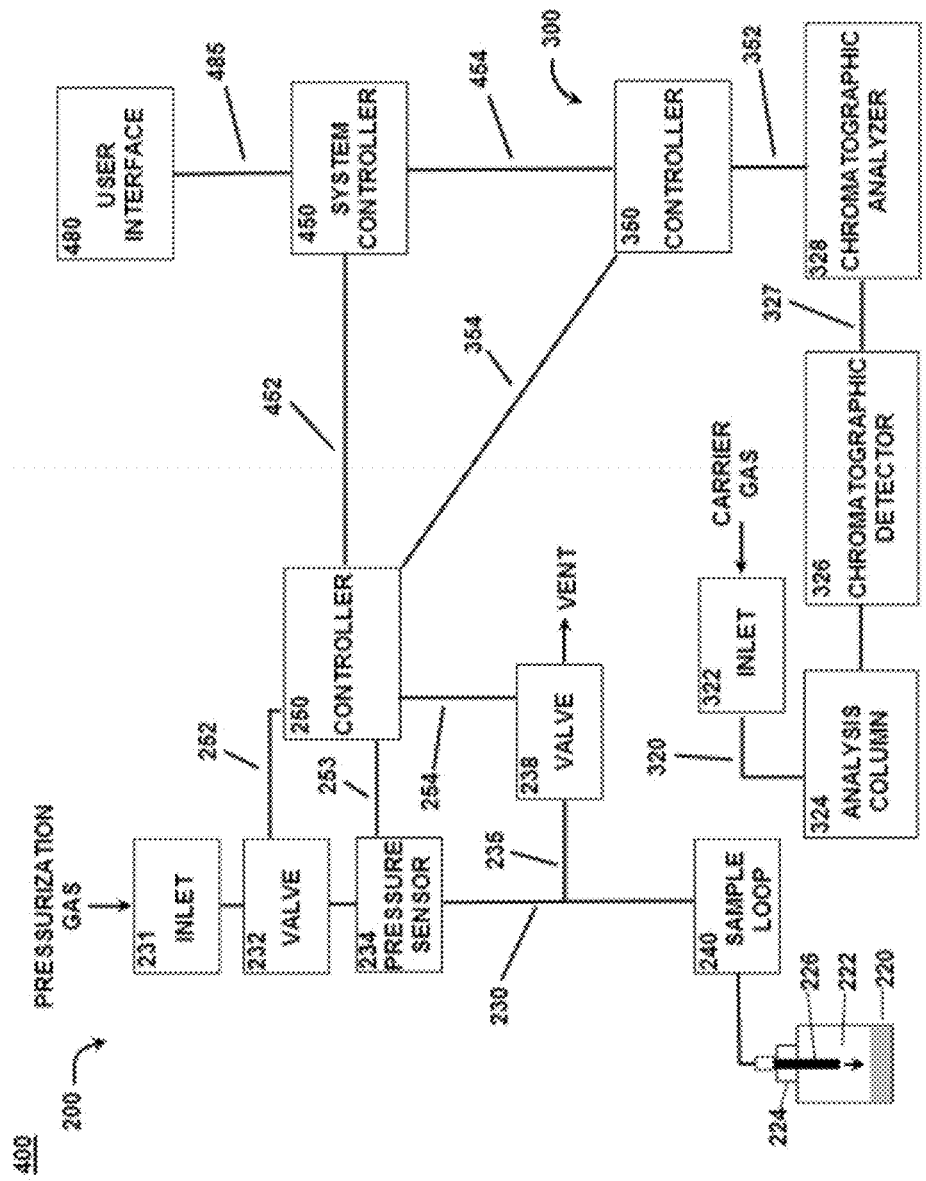
Figure 4B:
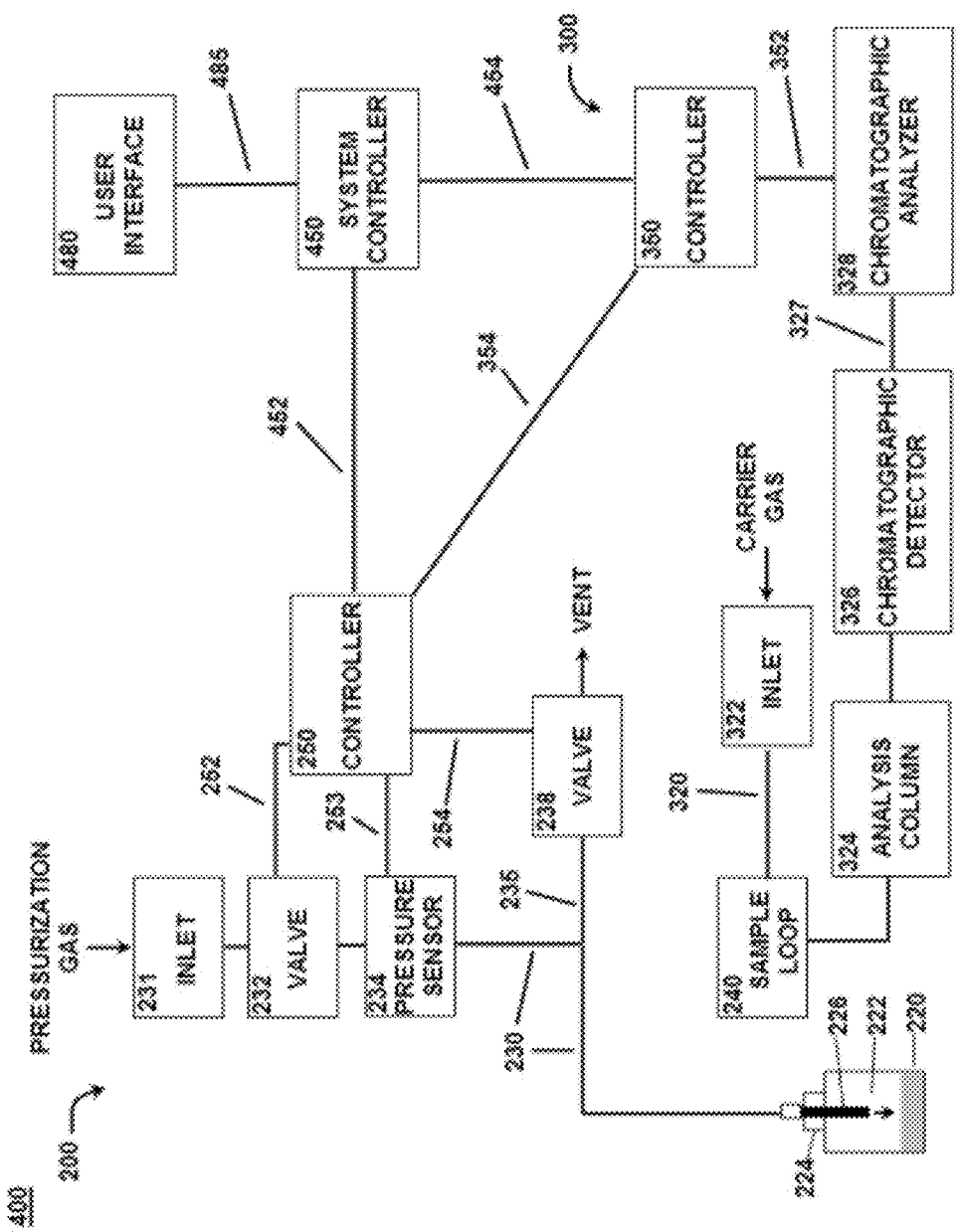

FIGS. 4A and 4B are schematic diagrams of an exemplary head space analysis system, as described herein. FIG. 4A depicts the configuration of the head space analysis system when the sample loop of the system is in fluid communication with the pressurization gas conduit and the vial containing the sample, as described herein. FIG. 4B depicts the configuration of the head space analysis system when the sample loop of the system is in fluid communication with the carrier gas conduit and the analysis column, as described herein.

FIGS. 5-8B include graphs and tables displaying experimental data obtained through practice and usage of the methods, devices, and systems disclosed herein. FIGS. 5-8B are described in further detail in the "Experimental Examples" section of the Detailed Description, which follows.

DETAILED DESCRIPTION

According to various embodiments, methods for controlling the rate of gas depressurization within a vial having a head space containing a gas sample are disclosed. In these embodiments, the gas sample within the head space of the vial is sampled by a head space sampling device. In some aspects, the head space sampling device can comprise a ventilation pathway connectable in fluid communication with a lower pressure environment, a sample loop connectable between and in fluid communication with the head space and the ventilation pathway, and a ventilation valve positioned in the ventilation pathway. The ventilation valve can be selectively adjustable to control the rate of gas flow from the head space through the sample loop to the lower pressure environment. The head space sampling device can further comprise means for establishing fluid communication between the sample loop and the head space.

In one aspect, the methods for controlling the rate of gas depressurization within the vial can comprise establishing fluid communication between the sample loop and the head space. In another aspect, the methods for controlling the rate of gas depressurization within the vial can comprise establishing a sample gas pressure within the head space. In this aspect, the sample gas pressure is greater than the pressure in the lower pressure environment. In an additional aspect, the methods for controlling the rate of gas depressurization within the vial can comprise connecting the sample loop in fluid communication with the lower pressure environment through the ventilation pathway. In a further aspect, the methods for controlling the rate of gas depressurization within the vial can comprise adjusting the ventilation valve so as to vent gas from the head space through the sample loop to the lower pressure environment at a predetermined rate, thereby allowing sample gas to flow from the head space to the sample loop.

In some aspects, the head space sampling device can comprise a ventilation pathway connectable in fluid communication with a lower pressure environment, a sample loop connectable between and in fluid communication with the head space and the ventilation pathway, and a ventilation valve positioned in the ventilation pathway, and a pressurization gas conduit having an inlet for receiving a pressurization gas. In these aspects, the pressurization gas conduit can optionally be connectable in fluid communication with the ventilation pathway and the sample loop.

In another aspect, the methods for controlling the rate of gas depressurization within the vial can comprise establishing fluid communication between the head space and the pressurization gas conduit. In another aspect, the methods for controlling the rate of gas depressurization within the vial can comprise pressurizing the pressurization gas conduit with the pressurization gas to establish a sample gas pressure within the head space. In this aspect, the sample gas pressure can be greater than the pressure in the lower pressure environment. In an additional aspect, the methods for controlling the rate of gas depressurization within the vial can comprise connecting the sample loop in fluid communication with the lower pressure environment through the ventilation pathway. In a further aspect, the methods for controlling the rate of gas depressurization within the vial can comprise monitoring the gas pressure within the head space of the vial. In still a further aspect, the methods for controlling the rate of gas depressurization within the vial can comprise adjusting the ventilation valve so as to vent gas from the head space through the sample loop to the lower pressure environment such that the gas pressure within the head space of the vial gradually decreases to a predetermined pressure setpoint, thereby allowing sample gas to flow from the head space to the sample loop in a desired manner.

A head space sampling device for sampling a gas sample from a head space of a vial is also disclosed. In one aspect, the head space sampling device can comprise a pressurization gas conduit having an inlet for receiving a pressurization gas. In this aspect, the pressurization gas conduit can be connectable in fluid communication with the head space of the vial. In an additional aspect, the head space sampling device can comprise a ventilation pathway connectable in fluid communication with a lower pressure environment. In another aspect, the head space sampling device can comprise a sample loop connectable between and in fluid communication with the head space and the ventilation pathway. In still another aspect, the head space sampling device can comprise means for establishing fluid communication between the head space of the vial and the sample loop. In a further aspect, the head space sampling device can comprise a ventilation valve positioned in the ventilation pathway and being selectively adjustable to control the rate of gas flow from the head space through the sample loop to the lower pressure environment. In yet another aspect, the head space sampling device can comprise a controller in communication with and adapted to adjust the ventilation valve to control the pressure within the head space. In this aspect, the controller can be adapted to adjust the ventilation valve such that gas is vented from the head space through the sample loop to the lower pressure environment at a predetermined rate.

According to various embodiments, head space analysis systems, which comprise a head space sampling device and a head space analyzer, are disclosed. In exemplary aspects, the head space analysis systems can sample and analyze a gas sample from a head space of a vial. A head space analyzer is configured to receive a fluid sample from the head space sampling device, send the fluid sample into an analysis apparatus for analysis, and detect and report the result of the analysis. The analysis apparatus can be a user-selectable component that is not supplied with the head space analyzer, for example, a gas chromatography column. Typically, a user chooses a column and fits it into the head space analyzer before operation of the analysis system. After the sample is analyzed by the gas chromatography column, the components of the sample pass through a detector in the head space analyzer for detection. In some embodiments, the head space analyzer may comprise a mass spectrometer. The sample can be directly analyzed and detected by a mass spectrometer without a separation step prior to mass spectrometry. Alternatively, the sample can be analyzed by a chromatography column first, followed by further analysis and detection by a mass spectrometer.

In one aspect, the head space sampling device of the head space analysis system can comprise a pressurization gas conduit having an inlet for receiving a pressurization gas. In this aspect, the pressurization gas conduit can be connectable in fluid communication with the head space of the vial. In another aspect, the head space sampling device of the head space analysis system can comprise a pressure sensor for measuring gas pressure within the pressurization gas conduit. In this aspect, the pressure sensor can be configured to generate a pressure signal indicative of the gas pressure within the pressurization gas conduit, and thus, the head space of the vial. In an additional aspect, the head space sampling device of the head space analysis system can comprise a ventilation pathway connectable in fluid communication with a lower pressure environment. In a further aspect, the head space sampling device of the head space analysis system can comprise a sample loop connectable between and in fluid communication with the head space and the ventilation pathway. In still another aspect, the head space sampling device of the head space analysis system can comprise a ventilation valve positioned in the ventilation pathway and being selectively adjustable to control the rate of gas flow from the head space through the sample loop to the lower pressure environment. In yet another aspect, the head space sampling device can comprise means for establishing fluid communication between the head space of the vial and the sample loop.

In yet another aspect, the head space sampling device of the head space analysis system can comprise a controller adapted to receive the pressure signal from the pressure sensor. In this aspect, the controller can be in communication with and control the ventilation valve by adjusting the ventilation valve to control the pressure within the pressurization gas conduit (and the head space). The controller can be adapted to compare the pressure signal from the pressure sensor to a predetermined pressure setpoint. The controller can be further adapted to adjust the ventilation valve such that the gas pressure within the pressurization gas conduit (and the head space) gradually decreases to the predetermined pressure setpoint. In still a further aspect, the head space analysis system can comprise a carrier gas conduit having an inlet for receiving a carrier gas. In another aspect, the sample loop can be connectable to allow fluid communication either between the head space and the ventilation pathway or between the carrier gas conduit and the head space analyzer.

The present invention can be understood more readily by reference to the following detailed description, examples, drawings, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

In this specification and in the claims that follow, reference will be made to a number of terms that shall be defined to have the following meanings:

As used throughout, the singular forms "a," "an" and "the" include plural referents unless the context clearly dictates otherwise. Thus, for example, reference to "a pressure sensor" can include two or more such pressure sensors unless the context indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

As used herein, the term "head space" refers to the portion of a vial or other container that is filled by gas. Thus, if a solid sample is positioned within the container, the head space will include the portion of the container that is filled by gaseous matter but will not include the portion of the container occupied by the solid sample. Similarly, if only gaseous matter is contained within the container, then the head space will include the entire contents of the container.

As used herein, the term "sample loop" refers to a container for a gas, liquid, or fluid sample. As described herein, a sample loop can be selectively placed in fluid communication with either of a head space sampling device and a head space analyzer. A sample loop is configured to receive at least a portion of a sample from a vial or other sample container in fluid communication with the head space sampling device. After receiving a portion of the sample from the sample container, the sample loop is configured to permit transfer of the sample to the head space analyzer. In some embodiments, the sample loop is configured to allow fluid communication between either the sample loop and the head space analyzer, or the sample loop and the ventilation pathway, but not both. As used herein, a sample loop can be, for example and without limitation, a conventional sample loop, a conventional sample trap, a conventional sample cell, and the like, such as the exemplary sample loops described herein.

As used herein, the term "vial" refers to any container that can contain a head space, with or without a gas, liquid, fluid, or solid sample. For example, and without limitation, the vial can be a conventional glass sample vial. As mentioned above, the space in the vial that is occupied by gas is the head space. It is contemplated that the vial can be configured to contain a head space and sample having a combined volume ranging from, for example, about 5 milliliters (mL) to about 22 milliliters (mL). However, any suitable volume for a particular head space and sample can be used as disclosed herein.

Figure 1:
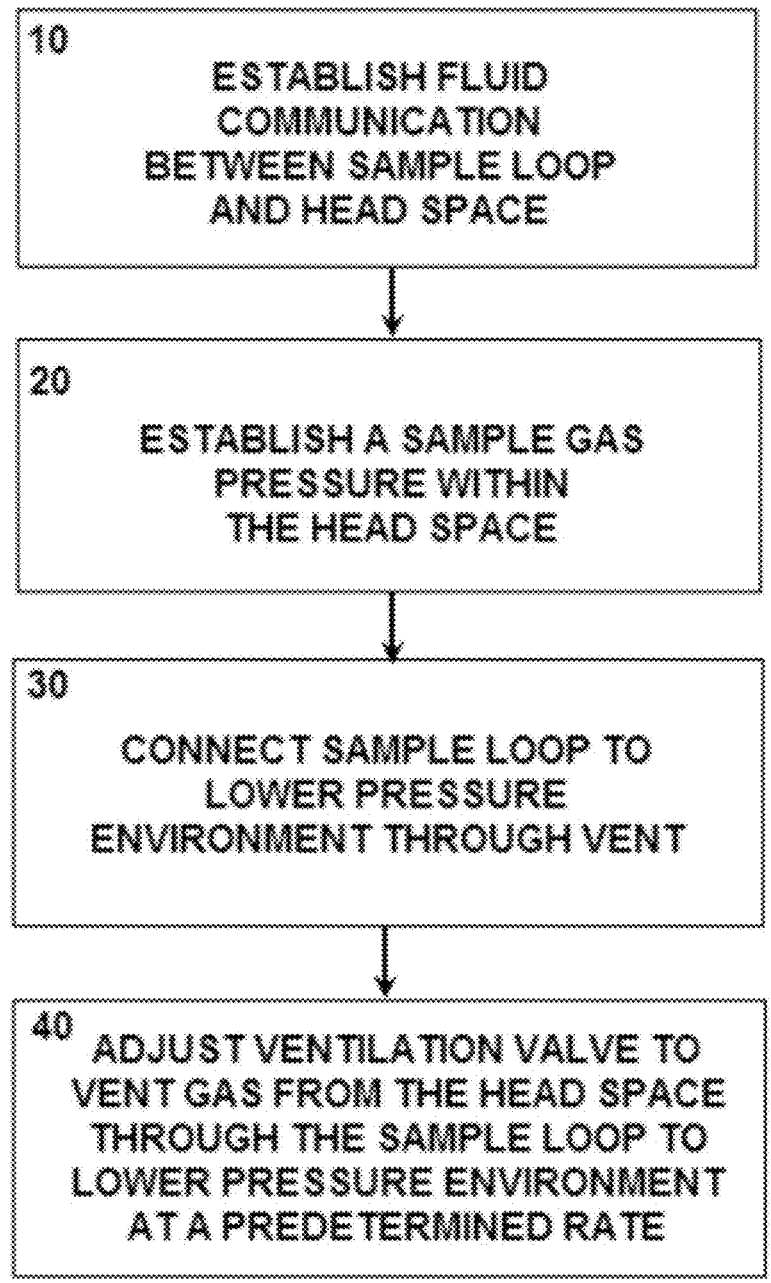
FIG. 1 is a flow chart depicting an exemplary method for controlling the rate of gas depressurization within a vial having a head space containing a gas sample to be sampled by a head space sampling device, as described herein.
Figure 2:
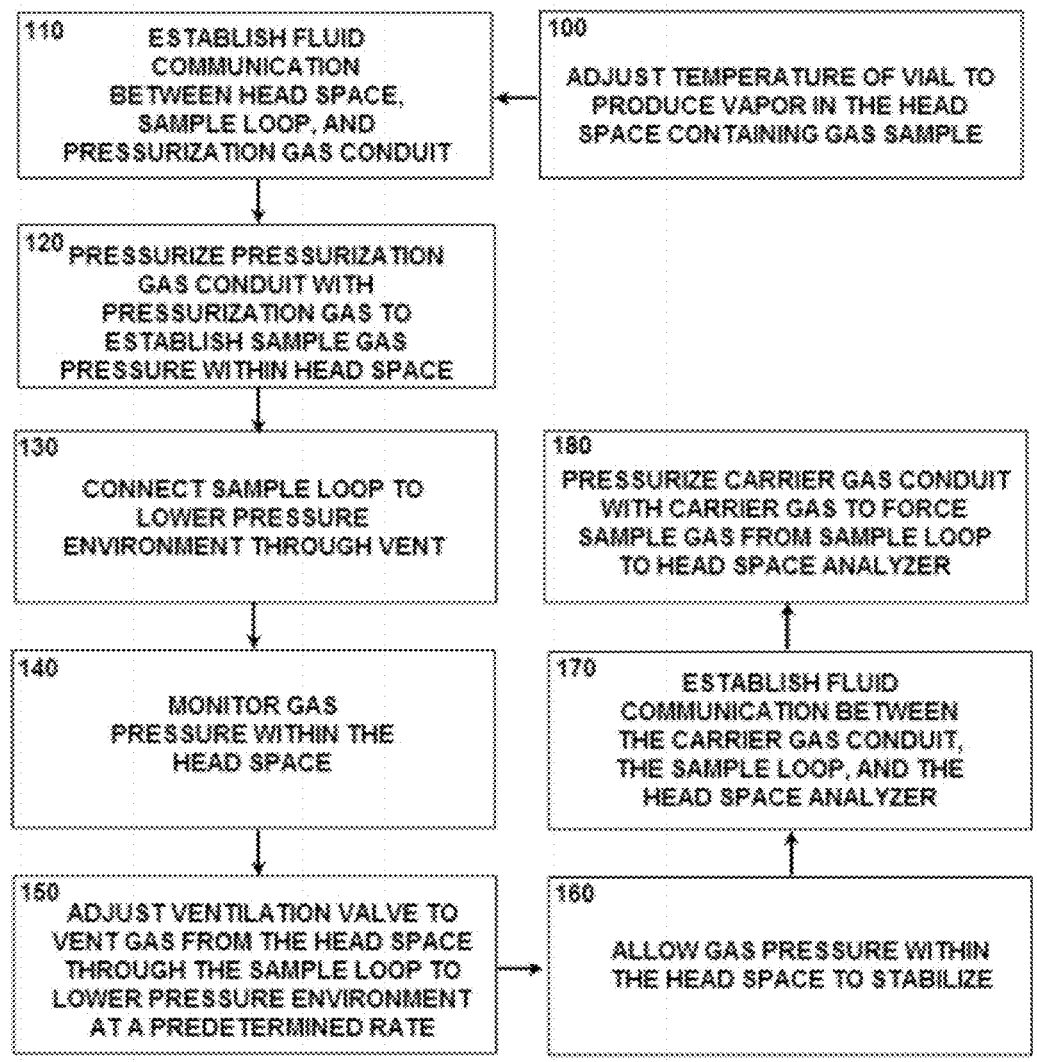
FIG. 2 is a flow chart depicting another exemplary method for controlling the rate of gas depressurization within a vial having a head space containing a gas sample to be sampled by a head space sampling device, as described herein.

Disclosed herein, and as shown in FIGS. 1-2, are methods for controlling the rate of gas depressurization within a vial having a head space containing a gas sample. As set forth below, the gas sample within the head space can be sampled by a head space sampling device. In exemplary aspects, the head space sampling device can comprise a ventilation pathway connectable in fluid communication with a lower pressure environment, a sample loop connectable between and in fluid communication with the head space and the ventilation pathway, and a ventilation valve positioned in the ventilation pathway. It is contemplated that the ventilation valve can be selectively adjustable to control the rate of gas flow from the head space through the sample loop to the lower pressure environment. It is further contemplated that the head space sampling device can comprise means for establishing fluid communication between the sample loop and the head space.

It is contemplated that the vial can be a conventional glass sample vial. It is further contemplated that the vial can be configured to contain a sample having a volume ranging from about 5 milliliters (mL) to about 22 milliliters (mL). It is still further contemplated that the pressurization gas can be any gas that is suitable for a particular sample. For example, the pressurization gas can be substantially non-reactive or inert for purposes of a particular sample. Thus, it is contemplated that the pressurization gas can be, for example and without limitation, helium gas, hydrogen gas, nitrogen gas, argon gas, and the like. In one exemplary aspect, it is contemplated that the pressurization gas can be a mixture of methane and argon, such as, for example and without limitation, 5% methane in argon.

In one exemplary aspect, it is contemplated that the sample loop can be attached to, or positioned within, a conventional valve for providing selective fluid communication between the sample loop and elements of the head space sampling device. For example, and without limitation, the sample loop can be attached to, or positioned within, a multi-port valve such as a six-port rotary valve, a multi-port diaphragm valve, and the like. It is further contemplated that the sample loop can be a part of a micro-machined electromechanical system comprising a plurality of multi-port valves or diaphragm valves. It is still further contemplated that the sample loop can be a conventional trap, such as those described herein.

It is contemplated that the lower pressure environment can be any pressure environment having a lower pressure than the post-pressurization pressure within the vial. For example, the lower pressure environment can be the ambient environment, a subambient pressure environment, or a pressure environment having a pressure greater than ambient pressure.

Figure 3:
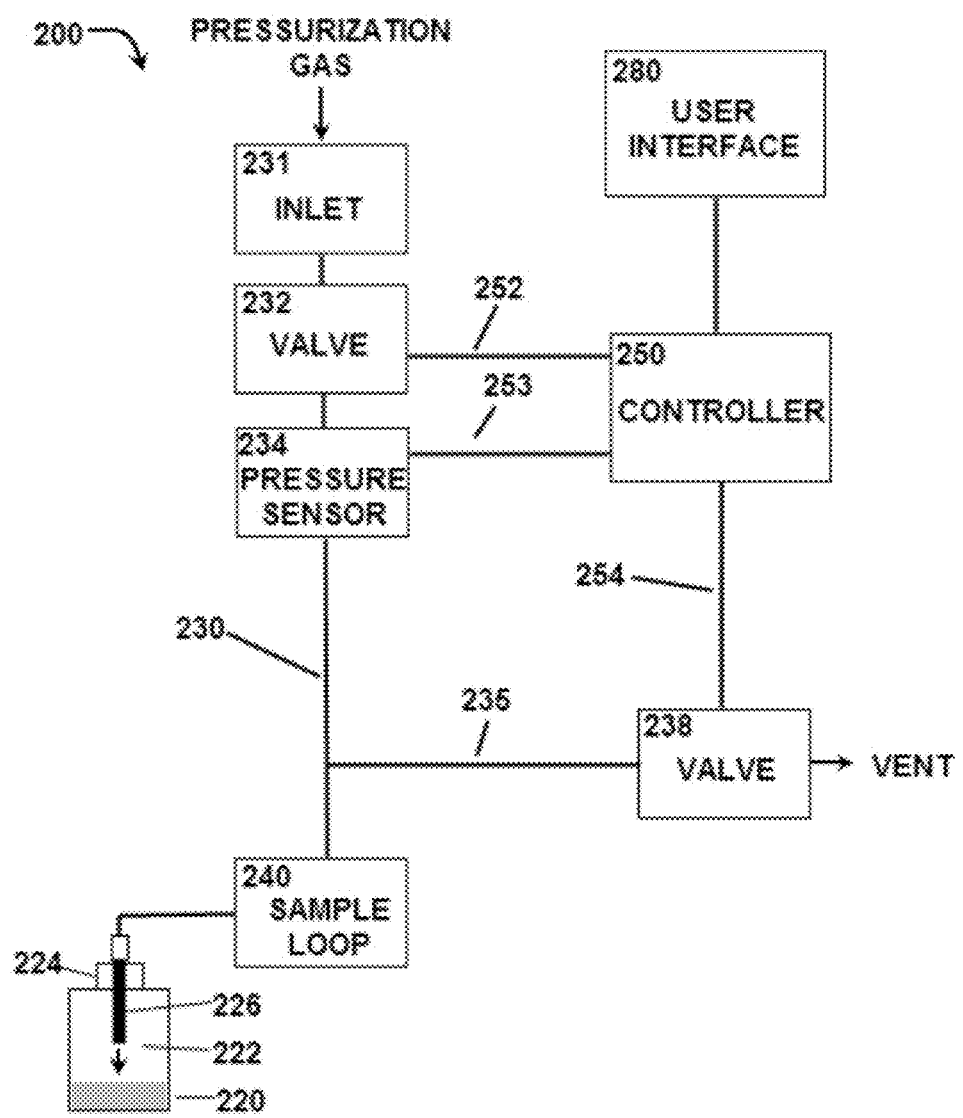
FIG. 3 is a schematic diagram of an exemplary head space sampling device, as described herein.

In exemplary aspects, it is contemplated that the head space sampling device can be a head space sampling device as disclosed herein, such as the head space sampling device disclosed in FIG. 3 and its corresponding description. It is further contemplated that the head space sampling device can be part of a head space analysis system as disclosed herein, such as the head space analysis system disclosed in FIGS. 4A-4B and its corresponding description.

As shown in FIG. 1, in one aspect, the method for controlling the rate of gas depressurization within the vial can comprise the step 10 of establishing fluid communication between the sample loop and the head space of the vial. In this aspect, it is contemplated that the step 10 of establishing fluid communication between the sample loop and the head space can comprise penetrating a septum of the vial with a needle or other suitable sample probe, such as a multi-port valve, having a bore in fluid communication with the sample loop, as described herein.

Optionally, in an additional aspect, the method for controlling the rate of gas depressurization within the vial can comprise the step of adjusting the temperature of the sample within the vial to produce a vapor in the head space. In this aspect, it is contemplated that the sample can be heated to produce the vapor in the head space. It is further contemplated that the head space can comprise a gaseous portion of the sample. In one exemplary aspect, it is contemplated that the temperature of the sample within the vial can be adjusted prior to the step 10 of establishing fluid communication between the sample loop and the head space. Alternatively, it is further contemplated that the temperature of the sample within the vial can be adjusted after the step 10 of establishing fluid communication between the sample loop and the head space.

In another aspect, as depicted in FIG. 1, the method for controlling the rate of gas depressurization within the vial can comprise the step 20 of establishing a sample gas pressure within the head space. In this aspect, the sample gas pressure can be greater than the pressure in the lower pressure environment. It is contemplated that the sample gas pressure can range from about 100 to about 800 kiloPascals (kPa). More preferably, the sample gas pressure can range from about 130 to about 310 kPa. In one exemplary aspect, the sample gas pressure can be about 200 kPa.

In an additional aspect, as shown in FIG. 1, the method for controlling the rate of gas depressurization within the vial can comprise the step 30 of connecting the sample loop in fluid communication with the lower pressure environment through the ventilation pathway.

As depicted in FIG. 1, in a further aspect, the method for controlling the rate of gas depressurization within the vial can comprise the step 40 of adjusting the ventilation valve so as to vent gas from the head space through the sample loop to the lower pressure environment. In this aspect, it is contemplated that the venting of gas from the head space through the sample loop to the lower pressure environment can allow sample gas to flow from the head space to the sample loop. Optionally, in one aspect, the ventilation valve can be adjusted so as to vent gas from the head space through the sample loop to the lower pressure environment at a predetermined rate. In this aspect, it is contemplated that the predetermined rate of venting gas from the head space through the sample loop to the lower pressure environment can range from about 0 to about 25 kPa per second (kPa/sec.), and more preferably from about 0.5 to about 6 kPa/sec. In one exemplary aspect, the predetermined rate of venting gas from the head space through the sample loop to the lower pressure environment can be about 2.3 kPa/sec. As used herein, the predetermined rate of venting gas from the head space through the sample loop to the lower pressure environment is indicative of the rate at which pressure is decreasing within the head space. Therefore, even though the predetermined rate of venting gas from the head space through the sample loop to the lower pressure environment is provided as a positive rate, this rate reflects a decreasing pressure within the head space of the vial.

In some aspects, the head space sampling device can further comprise a pressurization gas conduit that is connectable in fluid communication with the head space of the vial. In these aspects, the pressurization gas conduit can have an inlet for receiving a pressurization gas. It is contemplated that the pressurization gas can be any gas that is suitable for a particular sample. For example, the pressurization gas can be a gas that is substantially non-reactive or inert for purposes of a particular sample. Thus, it is contemplated that the pressurization gas can be, for example and without limitation, helium gas, hydrogen gas, nitrogen gas, argon gas, and the like. In one exemplary aspect, it is contemplated that the pressurization gas can be a mixture of methane and argon, such as, for example and without limitation, 5% methane in argon. In another aspect, it is contemplated that the pressurization gas conduit can be connectable in fluid communication with the ventilation pathway and with the sample loop.

As shown in FIG. 2, in one aspect, the method for controlling the rate of gas depressurization within the vial can comprise the step 110 of establishing fluid communication between the head space, the sample loop, and the pressurization gas conduit of the head space sampling device. In this aspect, it is contemplated that the step 110 of establishing fluid communication between the head space, the sample loop and the pressurization gas conduit can comprise penetrating a septum of the vial with a needle or other suitable probe having a bore in fluid communication with the sample loop, as described herein. It is contemplated that any arrangement of the head space, the sample loop, and the pressurization gas conduit is suitable for purposes of the disclosed methods, provided (1) the pressurization gas conduit is connectable in fluid communication with the head space of the vial and (2) the sample loop is connectable between and in fluid communication with the head space and the ventilation pathway. For example, although the some examples described and depicted herein indicate that the pressurization gas conduit is connectable in fluid communication with the ventilation pathway, it is also contemplated that the pressurization gas conduit and the ventilation pathway can be separately connectable in fluid communication with the head space.

Optionally, in an additional aspect, and as shown in FIG. 2, the method for controlling the rate of gas depressurization within the vial can comprise the step 100 of adjusting the temperature of the sample within the vial to produce a vapor in the head space. In this aspect, it is contemplated that the sample can be heated to produce the vapor in the head space. It is further contemplated that the head space can comprise a gaseous portion of the sample. In one exemplary aspect, it is contemplated that the temperature of the sample within the vial can be adjusted prior to the step 110 of establishing fluid communication between the head space, the sample loop, and the pressurization gas conduit. Alternatively, it is further contemplated that the temperature of the sample within the vial can be adjusted after the step 110 of establishing fluid communication between the head space, the sample loop and the pressurization gas conduit.

In another aspect, as depicted in FIG. 2, the method for controlling the rate of gas depressurization within the vial can comprise the step 120 of pressurizing the pressurization gas conduit with the pressurization gas to establish a sample gas pressure within the head space. In this aspect, the sample gas pressure can be greater than the pressure in the lower pressure environment. It is contemplated that the sample gas pressure can range from about 100 to about 800 kPa. More preferably, the sample gas pressure can range from about 130 to about 310 kPa. In one exemplary aspect, the sample gas pressure can be about 170 kPa. In another aspect, it is contemplated that the sample gas pressure can be set by a user of the head space sampling device.

In an additional aspect, as shown in FIG. 2, the method for controlling the rate of gas depressurization within the vial can comprise the step 130 of connecting the sample loop in fluid communication with the lower pressure environment through the ventilation pathway. In an additional aspect, the method for controlling the rate of gas depressurization within the vial can further comprise the step 140 of monitoring the gas pressure within the head space of the vial. It is contemplated that the step 140 of monitoring the gas pressure within the head space can be accomplished using a conventional pressure sensor positioned in fluid communication with the pressurization gas conduit. However, it is contemplated that the pressure sensor can be positioned anywhere within the head space sampling device that allows for monitoring of pressure substantially corresponding to the pressure within the head space of the vial.

As depicted in FIG. 2, in a further aspect, the method for controlling the rate of gas depressurization within the vial can comprise the step 150 of adjusting the ventilation valve so as to vent gas from the head space through the sample loop to the lower pressure environment. In this aspect, it is contemplated that the venting of gas from the head space through the sample loop to the lower pressure environment can allow sample gas to flow from the head space to the sample loop. Optionally, in one aspect, the ventilation valve can be adjusted so as to vent gas from the head space through the sample loop to the lower pressure environment at a predetermined rate. In this aspect, it is contemplated that the predetermined rate of venting gas from the head space through the sample loop to the lower pressure environment can range from about 0 to about 25 kPa/sec., and more preferably from about 0.5 to about 6 kPa/sec. In one exemplary aspect, the predetermined rate of venting gas from the head space through the sample loop to the lower pressure environment can be about 2.3 kPa/sec. It is contemplated that this controlled reduction in pressure can lead to greater control and/or reduction of gas flow through the sample loop and the ventilation pathway. Consequently, the controlled reduction in pressure can minimize any changes within the head space that are caused by the rapid expansions and high flow rates through the sample loop and the ventilation pathway that are associated with known methods and systems. As used herein, the predetermined rate of venting gas from the head space through the sample loop to the lower pressure environment is indicative of the rate at which pressure is decreasing with the head space. Therefore, even though the predetermined rate of venting gas from the head space through the sample loop to the lower pressure environment is provided as a positive rate, this rate reflects a decreasing pressure within the head space of the vial.

It is further contemplated that gas can be vented from the head space through the sample loop to the lower pressure environment at the predetermined rate such that the gas pressure within the head space gradually decreases to a predetermined pressure setpoint. It is still further contemplated that the predetermined pressure setpoint can range from about 100 to about 800 kPa, and more preferably from about 130 to about 310 kPa. In one exemplary aspect, the predetermined pressure setpoint can be about 170 kPa. In one aspect, it is contemplated that gas pressure within the head space can decrease substantially linearly. For example, when the predetermined pressure setpoint is an absolute pressure of 170 kPa, the sample gas pressure is 200 kPa, and the predetermined rate of venting gas from the sample loop to the lower pressure environment is 2 kPa per second (kPa/sec.), it is contemplated that the gas pressure within the head space can decrease substantially linearly for about 15 seconds until the predetermined pressure setpoint is achieved. In another aspect, it is contemplated that the gas pressure within the head space can decrease substantially exponentially. In addition to exponential and linear decreases in gas pressure within the head space, it is contemplated that the disclosed methods, systems, and devices can be used to create a decrease in gas pressure within the head space corresponding to any functional curve or sequence of curves, whether continuous or discontinuous, and whether linear or non-linear.

It is contemplated that in the absence of leaks, at any given time when the ventilation valve is closed, the measured pressure at any position between the ventilation pathway and the vial can be substantially equal to the gas pressure at any other position between the ventilation pathway and the vial, as well as the pressure within the vial. Where a pressure control valve is positioned within the pressurization gas conduit, the above relationship will hold true for any positions within the pressurization gas conduit that are positioned downstream of the pressure valve. When the ventilation valve is opened, it is contemplated that pressure gradients can be established within the head space sampling device. In one exemplary aspect, a pressure sensor that is used to measure the pressure of the head space within the vial can be positioned such that the pressure sensor does not contact the portions of the head space that are vented to the atmosphere through the sample loop. In this aspect, it is contemplated that the pressure sensor can be positioned in fluid communication with the pressurization conduit and spaced from the pathway followed by the head space during venting, as described herein. Therefore, in some aspects, it is contemplated that the gas pressure measured within the pressurization gas conduit can substantially correspond to the pressure within head space of the vial. However, it is contemplated that the pressure sensor can be positioned in any position within the head space sampling device where the pressure measured by the pressure sensor substantially corresponds to the pressure within the head space of the vial. In other aspects, two or more pressure sensors can be selectively positioned within the head space sampling device to provide one or more outputs indicative of the pressure within the head space of the vial.

Optionally, in another aspect, the head space sampling device can be connectable to a head space analyzer and a carrier gas conduit with an inlet for receiving a carrier gas. In this aspect, the sample loop can be connectable to allow fluid communication either between the head space and the ventilation pathway or between the carrier gas conduit and the head space analyzer. Thus, as depicted in FIG. 2, it is contemplated that the method for controlling the rate of gas depressurization within the vial can further comprise the step 170 of establishing fluid communication between the carrier gas conduit, the sample loop, and the head space analyzer. In one aspect, the step 170 of establishing fluid communication between the carrier gas conduit, the sample loop, and the head space analyzer can occur after the head space and/or sample loop of the head space sampling device is disconnected from the pressurization gas. In another aspect, the step 170 of establishing fluid communication between the sample loop and the head space analyzer can optionally occur during venting of gas from the head space through the sample loop to the lower pressure environment at the predetermined rate. It is contemplated that the period during which gas is vented at a predetermined rate from the head space through the sample loop to the lower pressure environment can correspond to a period of substantially constant gas flow through the sample loop. In a further aspect, the method for controlling the rate of gas depressurization within the vial can comprise the step 180 of pressurizing the carrier gas conduit with the carrier gas such that at least a portion of the sample gas within the sample loop is forced into the elements of the head space analyzer or an analysis apparatus connectable in communication with the head space analyzer, as described herein.

In exemplary aspects, the head space analyzer can comprise a chromatographic detector in fluid communication with an analysis apparatus, such as an analysis column. In these aspects, the analysis apparatus can be configured to receive the sample gas from the sample loop, and the chromatographic detector can be configured to produce an output signal indicative of the components within the head space. It is further contemplated that the head space analyzer can comprise a chromatographic analyzer adapted to receive and process the output signal from the chromatographic detector. In one aspect, the step of establishing fluid communication between the sample loop and the head space analyzer can comprise establishing fluid communication between the sample loop, the carrier gas conduit, and the analysis column.

A head space analyzer is configured to receive a fluid sample from the head space sampling device, send the fluid sample into an analysis apparatus for analysis, and detect and report the result of the analysis. The analysis apparatus can be a user-selectable component that is not supplied with the head space analyzer, for example, a gas chromatography column. Typically, a user chooses a column and fits it into the head space analyzer before operation of the analysis system. After the sample is analyzed by the gas chromatography column, the components of the sample pass through a detector in the head space analyzer for detection. In some embodiments, the head space analyzer may comprise a mass spectrometer. The sample can be directly analyzed and detected by a mass spectrometer without a separation step prior to mass spectrometry. Alternatively, the sample can be analyzed by a chromatography column first, followed by further analysis and detection by a mass spectrometer.

In a further aspect, as shown in FIG. 2, the method for controlling the rate of gas depressurization within the vial can optionally comprise the step 160 of allowing the gas pressure within the head space to substantially stabilize. In this aspect, it is contemplated that the period during which the gas pressure is substantially stable within the head space can correspond to a period of substantially zero gas flow through the pressurization gas conduit. It is further contemplated that the step 160 of allowing the gas pressure within the head space to substantially stabilize can occur prior to the step 170 of establishing fluid communication between the carrier gas conduit, the sample loop, and the head space analyzer. It is still further contemplated that the step 160 of allowing the gas pressure within the head space to substantially stabilize can comprise closing the ventilation valve.

As disclosed herein, it is contemplated that the gradual changes in pressure resulting from the controlled venting of gas from the head space through the sample loop to the lower pressure environment can improve the consistency and repeatability of gas sample concentrations that are delivered to the sample loop and transferred to the head space analyzer. Consequently, the consistency and repeatability in the analysis of a single gas sample or multiple gas samples can also be improved. For example, it is contemplated that through the use of the disclosed methods, the relative standard deviation of the area repeatability in the analysis of a particular gas sample can be less than about 5%, more preferably less than about 2%, and most preferably less than about 1%. Experimental examples of area repeatability for various samples are described herein.

It is contemplated that conventional processing techniques can be used to perform the steps of the methods disclosed herein. For example, it is contemplated that the disclosed method steps can be performed using conventional processing hardware, including, without limitation, a controller, a processor, a memory, a display, a user input mechanism such as a keyboard, and the like. It is further contemplated that the conventional processing hardware can be part of a conventional computer that can be used in conjunction with practicing the disclosed methods. In one aspect, the conventional processing hardware can be programmed by software to perform the steps of the disclosed methods.

Head space sampling devices that can be used to perform the steps of the previously described methods are also disclosed. Head space analysis systems comprising such head space sampling devices are also disclosed. As shown in FIG. 3, in exemplary aspects, the head space sampling device 200 can be configured to sample a gas sample from a head space 222 of a vial 220. It is contemplated that the vial 220 can be a conventional glass sample vial. It is further contemplated that the vial 220 can be configured to contain a head space 222 having a volume ranging from about 5 milliliters (mL) to about 22 milliliters (mL). In an additional aspect, it is contemplated that the vial 220 can comprise a septum 224. In this aspect, it is contemplated that the septum 224 can comprise a conventional elastomeric material, such as, for example and without limitation, rubber. It is further contemplated that the septum 224 can comprise Teflon®-coated silicone rubber.

In one aspect, as depicted in FIG. 3, the head space sampling device 200 can comprise a pressurization gas conduit 230 having an inlet 231 for receiving a pressurization gas. In this aspect, it is contemplated that the pressurization gas conduit 230 can be connectable in fluid communication with the head space 222 of the vial 220. It is further contemplated that the pressurization gas can be any gas that is suitable for a particular sample. For example, the pressurization gas can be substantially non-reactive or inert for purposes of a particular sample. Thus, it is contemplated that the pressurization gas can be, for example and without limitation, helium gas, hydrogen gas, nitrogen gas, argon gas, and the like. In one exemplary aspect, it is contemplated that the pressurization gas can be a mixture of methane and argon, such as, for example and without limitation, 5% methane in argon. In one aspect, the pressurization gas conduit 230 can have a valve 232 for controlling flow of gas therethrough the pressurization gas conduit 230. It is contemplated that the valve 232 of the pressurization gas conduit 230 can be a conventional electromechanical solenoid valve.

In an additional aspect, and with reference to FIG. 3, the head space sampling device 200 can comprise a pressure sensor 234 positioned in fluid communication with the pressurization gas conduit 230. In this aspect, the pressure sensor 234 can be configured to generate a pressure signal indicative of the gas pressure within the pressurization gas conduit 230. It is contemplated that the pressure sensor 234 can be a conventional piezoresistive pressure sensor. As described herein, it is contemplated that the pressure sensor 234 can be positioned anywhere within the head space sampling device 200 that allows for measurement of pressure substantially corresponding to the pressure within the head space 222 of the vial 220.

In an additional aspect, as shown in FIG. 3, the head space sampling device 200 can comprise a ventilation pathway 235 connectable in fluid communication with a lower pressure environment. In one exemplary aspect, it is contemplated that the ventilation pathway 235 can be coupled to the pressurization gas conduit 230 downstream of the inlet 231 to the pressurization gas conduit 230. It is further contemplated that the lower pressure environment can be any pressure environment having a lower pressure than the post-pressurization pressure within the vial 220. For example, the lower pressure environment can be the ambient environment, a subambient pressure environment, or a pressure environment having a pressure greater than ambient pressure but less than the post-pressurization pressure within the head space 222 of the vial 220.

As shown in FIG. 3, in another aspect, the head space sampling device 200 can comprise a sample loop 240 connectable in fluid communication with the head space 222 and the ventilation pathway 235. In one exemplary aspect, it is contemplated that the sample loop 240 can be attached to, or positioned within, a conventional valve for providing selective fluid communication between the sample loop and elements of the head space sampling device 200. For example, and without limitation, the sample loop 240 can be attached to, or positioned within, a multi-port valve such as a six-port rotary valve, a multi-port diaphragm valve, and the like. It is further contemplated that the sample loop 240 can be a part of a micro-machined electromechanical system comprising a plurality of multi-port valves or diaphragm valves. It is still further contemplated that the sample loop 240 can be a conventional chemical trap, such as those described herein.

The exemplary configuration of pressurization gas conduit 230, ventilation pathway 235, and sample loop 240 is only one potential configuration of these elements of the head space sampling device 200. It is contemplated that any configuration of the pressurization gas conduit 230, the ventilation pathway 235, and the sample loop 240 is acceptable for purposes of the disclosed methods, systems, and devices, provided (1) the pressurization gas conduit is connectable in fluid communication with the head space 222 of the vial 220 and (2) the sample loop is connectable between and in fluid communication with the head space of the vial and the ventilation pathway.

In an additional aspect, as depicted in FIG. 3, it is contemplated that the head space sampling device 200 can comprise means for establishing fluid communication between the sample loop 240 and the vial 220 containing the head space 222. In one aspect, the means for establishing fluid communication between the sample loop 240 and the head space 222 can comprise a needle 226 having a bore in fluid communication with the sample loop. In this aspect, it is contemplated that the septum 224 can be configured to form a seal around the needle 226 upon insertion of the needle into the head space 222 of the vial 220. It is contemplated that any conventional means for establishing fluid communication can be used to establish fluid communication between the sample loop 240 and the head space 222. For example and without limitation, the means for establishing fluid communication between the sample loop 240 and the vial 220 containing the head space 222 can comprise a stream selection valve for selective sampling through multiple vessels, as well as resealable valves for attachment to the vial.

As depicted in FIG. 3, in a further aspect, the head space sampling device 200 can comprise a ventilation valve 238 positioned in the ventilation pathway 235 and being selectively adjustable to control the rate of gas flow from the head space 222 through the sample loop 240 to the lower pressure environment. In this aspect, it is contemplated that the ventilation valve 238 can be opened and closed to provide selective fluid communication between the head space 222 and the sample loop 240 and the lower pressure environment. In one exemplary aspect, the ventilation valve 238 can be a conventional proportional valve, such as, for example and without limitation, an electromechanical proportional valve.

It is contemplated that in the absence of leaks, at any given time when the ventilation valve 238 is closed, the measured pressure at any position between the ventilation pathway 235 and the vial 220 can be substantially equal to the gas pressure at any other position between the ventilation pathway and the vial, as well as the pressure within the head space 222 of the vial. Where a pressure valve 232 is positioned within the pressurization gas conduit 230, the above relationship will hold true for any positions within the pressurization gas conduit that are positioned downstream of the pressure valve. When the ventilation valve 238 is opened, it is contemplated that pressure gradients can be established within the head space sampling device 200. In one exemplary aspect, the pressure sensor 234 that is used to measure the pressure of the head space 222 within the vial 220 can be positioned such that the pressure sensor does not contact the portions of the head space that are vented to the atmosphere through the sample loop 240 and the ventilation pathway 235. In this aspect, it is contemplated that the pressure sensor 234 can be positioned in fluid communication with the pressurization conduit 230 and spaced from the pathway followed by the head space 222 during venting, as described herein. Therefore, it is contemplated that the gas pressure measured within the pressurization gas conduit 230 can substantially correspond to the pressure within head space 222 of the vial 220. However, it is contemplated that the pressure sensor 234 can be positioned in any position within the head space sampling device 200 where the pressure measured by the pressure sensor substantially corresponds to the pressure within the head space 222 of the vial 220. In other aspects, the head space sampling device 200 can comprise two or more pressure sensors that are selectively positioned within the head space sampling device to provide one or more outputs indicative of the pressure within the head space 222 of the vial 220.

Optionally, in one aspect, the head space sampling device 200 can comprise a conventional chemical trap (not shown). In this aspect, it is contemplated that the chemical trap can be positioned within the pressurization gas conduit 230 between the ventilation pathway and the sample loop 240. It is further contemplated that the chemical trap can prevent portions of the sample from escaping to the lower pressure environment through the ventilation valve 238 and/or damaging the ventilation valve.

Optionally, in another aspect, although not depicted in FIG. 3, the head space sampling device 200 can comprise means for adjusting the temperature of the sample within the vial 220. It is contemplated that the means for adjusting the temperature of the sample can comprise any conventional mechanism for controlling temperature, including, for example and without limitation, a hot plate, a traditional oven, a convection oven, a burner, a water bath, an oil bath, a cartridge heater, a heating mantle, a Peltier device, and the like.

In yet another aspect, as shown in FIG. 3, the head space sampling device 200 can comprise a controller 250 in communication with and adapted to adjust the ventilation valve 238 to control the pressure within the head space 222. In this aspect, the controller 250 can be adapted to adjust the ventilation valve 238 such that gas is vented from the head space 222 through the sample loop 240 to the lower pressure environment at a predetermined rate. It is contemplated that the predetermined rate of venting of the gas from the head space 222 through the sample loop 240 to the lower pressure environment can range from about 0 to about 25 kPa/sec., and more preferably from about 0.5 to about 6 kPa/sec. In one exemplary aspect, the predetermined rate of venting of the gas from the head space 222 through the sample loop 240 to the lower pressure environment can be about 2.3 kPa/sec. As used herein, the predetermined rate of venting gas from the head space 222 through the sample loop 240 to the lower pressure environment is indicative of the rate at which pressure is decreasing within the head space. Therefore, even though the predetermined rate of venting gas from the head space 222 through the sample loop 240 to the lower pressure environment is provided as a positive rate, this rate reflects a decreasing pressure within the head space of the vial 220.

In a further aspect, the controller 250 can be adapted to receive the pressure signal from the pressure sensor 234. In this aspect, it is contemplated that the controller 250 can be adapted to compare the pressure signal from the pressure sensor 234 to a predetermined pressure setpoint. In an additional aspect, the controller 250 can be further adapted to adjust the ventilation valve 238 such that the gas pressure within the head space 222 gradually decreases from an initial sample gas pressure to the predetermined pressure setpoint. It is contemplated that the predetermined pressure setpoint can range from about 100 to about 800 kPa, and more preferably from about 130 to about 310 kPa. In one exemplary aspect, the predetermined pressure setpoint can be about 170 kPa.

Although the ranges for the monitored pressures and predetermined pressure setpoints disclosed herein are referenced to absolute pressures, it is contemplated that the monitored pressures and predetermined pressure setpoints can also be referenced to a standard atmosphere (101.3 kPa) or to ambient pressure. Thus, it is contemplated that the pressure sensor 234 within the pressurization gas conduit 230 can be one of an absolute pressure sensor (referenced to vacuum), a sealed sensor (referenced to a standard atmosphere), and a sensor referenced to the current ambient pressure. It is further contemplated that desired analytical repeatability can be obtained when the absolute pressure values are substantially constant from sample to sample. When the pressure sensor 234 is an absolute pressure sensor, the output of the pressure sensor can be used directly as a control pressure value, which, as used herein, corresponds to the desired setpoint pressure of the pressurization gas conduit 230. When the pressure sensor 234 is a sealed sensor referenced to one standard atmosphere, the absolute pressure is substantially equal to the measured pressure within the pressurization gas conduit plus 101.3 kPa; however, this relationship only holds at a specific temperature. Therefore, when the pressure sensor 234 is a sealed sensor referenced to one standard atmosphere, the head space sampling device can be configured to correct for changes in the temperature of the pressure sensor. When the pressure sensor 234 is referenced to ambient pressure, the absolute pressure is equal to the sum of the measured pressure within the pressurization gas conduit and the ambient pressure. Because ambient pressure is not constant in time or in location, constant absolute pressures cannot be achieved by keeping the indicated pressure constant. Thus, although not shown in FIG. 3, when the pressure sensor 234 is referenced to ambient pressure, the head space sampling device can include at least one absolute pressure sensor for measuring the ambient pressure. The measurements retrieved by the controller 250 from pressure sensor 234 and the absolute pressure sensor can then be used to calculate the corresponding control pressure value.

As further depicted in FIG. 3, the controller 250 can receive the pressure signal from the pressure sensor 234 through electrical communication link 253. In an additional aspect, it is contemplated that the controller 250 can control, and be in communication with, the ventilation valve 238 of the pressurization gas conduit 230. In this aspect, the controller 250 can be configured to open and close the ventilation valve 238 to control at least one of the pressures within and the flow through one or more of the head space 222, the pressurization gas conduit 230, and other elements of the head space analysis device. As depicted in FIG. 3, the controller 250 can communicate with the ventilation valve 238 of the pressurization gas conduit 230 through electrical communication link 254. In a further aspect, the controller 250 can control, and be in communication with, the valve 232 of the pressurization gas conduit 230. In this aspect, the controller 250 can be configured to open and close the valve 232 to further control at least one of the pressures within and the flow through one or more of the head space 222, the pressurization gas conduit 230, and other elements of the head space analysis device. As depicted in FIG. 3, the controller 250 can communicate with the valve 232 of the pressurization gas conduit 230 through electrical communication link 252. It is contemplated that electrical communication links 252, 253, and 254 can comprise any conventional means for electrical communication, including, for example and without limitation, conventional wires and conventional wireless transmission mechanisms, including, for example and without limitation, radio frequency (RF) communication mechanisms and infrared (IR) communication mechanisms.

In an additional aspect, the controller 250 of the head space sampling device 200 can be adapted to provide an output indicative of at least one of gas pressure within the head space 222 and change in gas pressure within the head space. In this aspect, it is contemplated that the controller 250 can be adapted to produce an alert to symbolize whether the predetermined pressure setpoint and/or the predetermined rate of venting gas from the head space 222 through the sample loop 240 to the lower pressure environment have been achieved. In one exemplary aspect, it is contemplated that the pressure of the head space 222 can substantially correspond to the measured pressure within the pressurization gas conduit 230. In another aspect, it is contemplated that the controller 250 can be a single device or a plurality of devices connected in electrical communication with one another.

In a further aspect, the controller 250 of the head space sampling device 200 can be in electrical communication with the means for adjusting the temperature of the sample within the vial 220. In this aspect, it is contemplated that the controller 250 can be selectively programmed by a user to adjust the temperature of the sample in a desired manner.

In another aspect, the head space sampling device 200 can comprise a conventional user interface 280, such as, for example and without limitation, a computer having a keyboard and a monitor. In this aspect, the user interface 280 of the head space sampling device 200 can be in electrical communication with the controller 250. In one aspect, the user interface 280 can be configured to display the output of the controller 250. In another aspect, the user interface 280 can be configured to receive at least one input from a user of the head space sampling device 200. In this aspect, it is contemplated that the at least one input from the user can comprise instructions for operation of the head space sampling device 200 that are responsive to the output of the controller 250. It is further contemplated that the at least one input from the user can comprise instructions for operation of the head space sampling device 200, including, for example and without limitation, selected gas pressures to be achieved and/or maintained within the head space 222 and selected rates of venting gas from the head space 222 through the sample loop 240 to the lower pressure environment.

In one exemplary aspect, at least one of the user interface 280 and the controller 250 of the head space sampling device 200 can have a memory for storing data files corresponding to respective samples. In this aspect, where the output of the controller 250 of the head space sampling device 200 is indicative of a failure to achieve the predetermined pressure setpoint and/or the predetermined rate of venting gas from the head space 222 through the sample loop 240 to the lower pressure environment, it is contemplated that the controller 250 can be configured to store a failure entry in the memory of at least one of the user interface 280 and the controller. Where the output of the controller 250 is indicative of a failure to achieve the predetermined pressure setpoint and/or the predetermined rate of venting gas from the head space 222 through the sample loop 240 to the lower pressure environment, it is further contemplated that the controller 250 can be configured to flag the corresponding data file in the memory of at least one of the user interface 280 and the controller. It is still further contemplated that, where the output of the controller 250 is indicative of a failure to achieve the predetermined pressure setpoint and/or the predetermined rate of venting gas from the head space 222 through the sample loop 240 to the lower pressure environment, the user of the head space sampling device 200 can enter an input into the user interface 280 to indicate whether sampling and/or analysis of particular samples should continue. For example, where the head space sampling device 200 is configured to sample the head spaces 222 of a sequence of different vials 220, the user can enter an input into the user interface 280 to indicate whether or not the head space sampling device should continue with sequential sampling and/or analysis of the head spaces of the vials.

In some aspects, the controller 250 can comprise a processor. In this aspect, the processor can be programmed to operate in accordance with at least one of software, firmware, and field-programmable gate array (FPGA) code. It is contemplated that the controller 250 can comprise a memory that is configured to store the software, firmware, and FPGA code that control the operation of the processor. Alternatively, the controller 250 can be in communication with an external computer that stores the software, firmware and FPGA code. In one aspect, at least one of the software, firmware, and FPGA code can instruct the controller 250 to determine whether the predetermined pressure setpoint and/or the predetermined rate of venting gas from the head space 222 through the sample loop 240 to the lower pressure environment are achieved, as disclosed herein. In an additional aspect, the controller 250, can be configured to log the failure to achieve the predetermined pressure setpoint and/or the predetermined rate of venting gas from the head space 222 through the sample loop 240 to the lower pressure environment in the memory. In this aspect, it is contemplated that the log of such a failure can enable a user of the system to identify results that should not be included in the analysis of the sample. In another aspect, at least one of the software, firmware, and FPGA code can instruct the controller 250 to respond in a predetermined manner to a failure to achieve the predetermined pressure setpoint and/or the predetermined rate of venting gas from head space 222 through the sample loop 240 to the lower pressure environment. In this aspect, it is contemplated that the predetermined manner of responding to detection of such a failure can comprise at least one of: prompting a user for instructions; aborting the analysis of the sample and advancing to the next sample; proceeding with analysis of the sample; aborting all analysis of the sample; activating an alarm; sending an alert e-mail to desired recipients; opening at least one valve within the head space sampling device 200; and closing at least one valve within the head space sampling device. In a further aspect, it is contemplated that the controller 250 can be in communication with a keyboard. In this aspect, a user can use the keyboard to enter information for processing by the controller 250. In still a further aspect, the controller 250 can be in communication with a conventional display. In this aspect, the controller 250 can be configured to display the outputs disclosed herein.

In other aspects, and as depicted in FIGS. 4A-4B, the head space sampling device 200 can be in communication with a head space analyzer 300 to form a head space analysis system 400 for analyzing a gas sample from a head space 222 of a vial 220. It is contemplated that the head space analyzer 300 of the head space analysis system 400 can comprise any analytical device that can make measurements of gaseous samples, including, for example and without limitation, a gas chromatograph, a mass spectrometer, a gas phase infrared spectrometer, a sensor array, and the like. In an exemplary aspect, it is contemplated that when the analyzer 300 comprises a gas chromatograph, the sample can also be trapped either in a cold temperature programmable inlet or on the head of a separation column at low temperature. In this aspect, it is contemplated that a head space from a single sample can be sampled multiple times and concentrated in the inlet or on the column. Similarly, it is contemplated that a single sample can be placed in multiple head space vials and each vial can be sampled using the head space sampling device one or more times, with the head space samples trapped in the inlet or on the column. These samples can then be desorbed thermally using conventional methods. It is contemplated that these methods can provide additional sample concentration.

In another aspect, it is contemplated that the head space analyzer 300 can be configured to trap the head space components of the vial 220 in a chemical trap, such as, for example and without limitation, activated charcoal, Tenax®, cold finger, and the like. In this aspect, the trapped head space components can be desorbed thermally into the gas phase or by a liquid using conventional methods. It is further contemplated that, where the head space is desorbed in a liquid as described, the head space analyzer 300 can comprise any analytical device that can make measurements of liquid samples, including, for example and without limitation, a high performance liquid chromatograph, a liquid spectrometer, and the like.

In some aspects, the head space analyzer 300 can be configured to analyze a sample from the head space 222 of the vial 220. More specifically, the head space analyzer 300 can be configured to receive a head space sample from the head space sampling device 200, send the head space sample into an analysis apparatus for analysis, and detect and report the result of the analysis. The analysis apparatus can be a user-selectable component that is not supplied with the head space analyzer, for example, a gas chromatography column. Typically, a user chooses a column and fits it into the head space analyzer 300 before operation of the analysis system 400. After the sample is analyzed by the gas chromatography column, the components of the sample pass through a detector in the head space analyzer 300 for detection. In some embodiments, the head space analyzer 300 may comprise a mass spectrometer. The sample can be directly analyzed and detected by a mass spectrometer without a separation step prior to mass spectrometry. Alternatively, the sample can be analyzed by a chromatography column first, followed by further analysis and detection by a mass spectrometer.

As shown in FIGS. 4A-4B, in one aspect, the head space analysis system 400 can comprise a carrier gas conduit 320. In this aspect, the carrier gas conduit 320 can have an inlet 322 for receiving a carrier gas. Like the pressurization gas, it is contemplated that the carrier gas can be any gas that is substantially non-reactive or inert for purposes of a particular sample. Thus, it is contemplated that the carrier gas can be, for example and without limitation, helium gas, hydrogen gas, nitrogen gas, argon gas, and the like. In one exemplary aspect, it is contemplated that the carrier gas can be a mixture of methane and argon, such as, for example and without limitation, 5% methane in argon.

In one exemplary aspect, as shown in FIGS. 4A-4B, the analysis apparatus can comprise an analysis column 324, such as, for example and without limitation, a chromatography column. In a further aspect, the detector of the head space analyzer 300 can comprise a chromatographic detector 326. In this aspect, the chromatographic detector 326 can be in fluid communication with the analysis column 324. It is contemplated that the chromatographic detector can be configured to produce an output signal indicative of the components of the head space 222 within the vial 220. In still a further aspect, the head space analyzer 300 can comprise a chromatographic analyzer 328 adapted to receive and process the output signal from the chromatographic detector 326. As depicted in FIGS. 4A-4B, the chromatographic detector 326 can communicate with the chromatographic analyzer 328 through electrical communication link 327. In yet another aspect, the head space analyzer 300 can comprise a controller 350 as described herein. In this aspect, the controller 350 can control, and communicate with, the components of the head space analyzer, such as the chromatographic analyzer 328, through an electrical communication link 352. It is contemplated that electrical communication links 327 and 352 can comprise any conventional means for electrical communication, including, for example and without limitation, conventional wires and conventional wireless transmission mechanisms, including, for example and without limitation, radio frequency (RF) communication mechanisms and infrared (IR) communication mechanisms. Although not shown in FIGS. 4A-4B, it is contemplated that controllers 250 and 350 can be in communication with one or more user interfaces as described herein.

In these aspects, it is contemplated that the sample loop 240 of the head space sampling device 200 is connectable to allow fluid communication either between the ventilation pathway 235 and the head space 222 or between the sample loop 240 and the head space analyzer 300. As shown in FIGS. 4A-4B, in one aspect, the sample loop 240 is connectable to allow fluid communication either between the ventilation pathway 235 and the head space 222 or between the carrier gas conduit 320 and the analysis column 324. In exemplary aspects, as depicted in FIGS. 4A-4B, the pressurization gas conduit 230 is connectable in fluid communication with the ventilation pathway 235, and the sample loop 240 of the head space sampling device 200 is connectable to establish communication between the head space 222 and both the pressurization gas conduit 230 and the ventilation pathway 235. Thus, in these aspects, the sample loop 240 is connectable to allow fluid communication either between the pressurization gas conduit 230 and the head space 222 or between the sample loop 240 and the head space analyzer 300. As shown in FIGS. 4A-4B, in one aspect, the sample loop 240 is connectable to allow fluid communication either between the pressurization gas conduit 230 and the head space 222 or between the carrier gas conduit 320 and the analysis column 324. As depicted in FIG. 4A, when the pressurization gas conduit 230 is connected to the sample loop 240, pressurization gas flows through the pressurization gas conduit 230, through the sample loop 240, and into the vial 220. As depicted in FIG. 4B, when the carrier gas conduit 320 is connected to the sample loop 240, carrier gas flows through the carrier gas conduit, through the sample loop, and into the analysis column 324. As depicted in FIG. 4A, when the pressurization gas conduit 230 is connected to the sample loop 240, the carrier gas conduit 320 is not in fluid communication with the sample loop.

Optionally, in another aspect, and as shown in FIGS. 4A-4B, the head space analysis system 400 can comprise a system controller 450. In this aspect, it is contemplated that the system controller 450 can be in communication with at least one of the controller 250 of the head space sampling device 200 and the controller 350 of the head space analyzer 300 to thereby provide overall control over the head space analysis system 400. It is contemplated that the system controller 450 can be in communication with the controller 250 of the head space sampling device 200 through electrical communication link 452. It is further contemplated that the system controller 450 can be in communication with the controller 350 of the head space analyzer 300 through electrical communication link 454. It is still further contemplated that the system controller 450 can be any conventional electrical communication system that is configured to communicate with the head space sampling device 200 and the head space analyzer 300, such as a controller as described herein. In one aspect, controller 250 of the head space sampling device 200 can be in communication with the controller 350 of the head space analyzer 300 through electrical communication link 354. It is contemplated that electrical communication links 354, 452, and 454 can comprise any conventional means for electrical communication, including, for example and without limitation, conventional wires and conventional wireless transmission mechanisms, including, for example and without limitation, radio frequency (RF) communication mechanisms and infrared (IR) communication mechanisms.

In an additional aspect, as shown in FIGS. 4A-4B, the system controller 450 can be in communication with a user interface 480, as described herein, through electrical communication link 485. It is contemplated that electrical communication link 485 can comprise any conventional means for electrical communication, including, for example and without limitation, conventional wires and conventional wireless transmission mechanisms, including, for example and without limitation, radio frequency (RF) communication mechanisms and infrared (IR) communication mechanisms. It is further contemplated that the user interface 480 can be configured to display an output of the system controller 450. In another aspect, it is contemplated that the user interface 480 can be configured to receive at least one input from a user of the head space analysis system 400. In this aspect, it is contemplated that the at least one input from the user can comprise instructions for operation of the head space sampling device 200, such as instructions that are responsive to the output of the system controller 450. It is further contemplated that the at least one input from the user can comprise instructions for operation of the head space analyzer 300, such as instructions that are responsive to the output of the system controller 450. In one exemplary aspect, the user interface 480 of the head space analysis system 400 can have a memory for storing data files corresponding to respective samples. In this aspect, the user interface 480 can be configured to associate outputs from the head space sampling device 200 and the head space analyzer 300 that result from the sampling and analysis of a particular sample.

As disclosed herein, it is contemplated that the gradual changes in pressure resulting from the controlled venting of gas from the head space 222 through the sample loop 240 to the lower pressure environment can improve the consistency and repeatability of gas sample concentrations that are delivered to the sample loop and transferred to the head space analyzer 300. Consequently, the consistency and repeatability in the analysis of a single gas sample or multiple gas samples can also be improved. For example, it is contemplated that through the use of the disclosed methods, the relative standard deviation of the area repeatability in the analysis of a particular gas sample can be less than about 5%, more preferably less than about 2%, and most preferably less than about 1%. Experimental examples of area repeatability for various samples are described herein.

EXPERIMENTAL EXAMPLES

The following experimental examples describe data obtained through practice and usage of exemplary methods, devices, and systems as disclosed herein.

Figure 5:
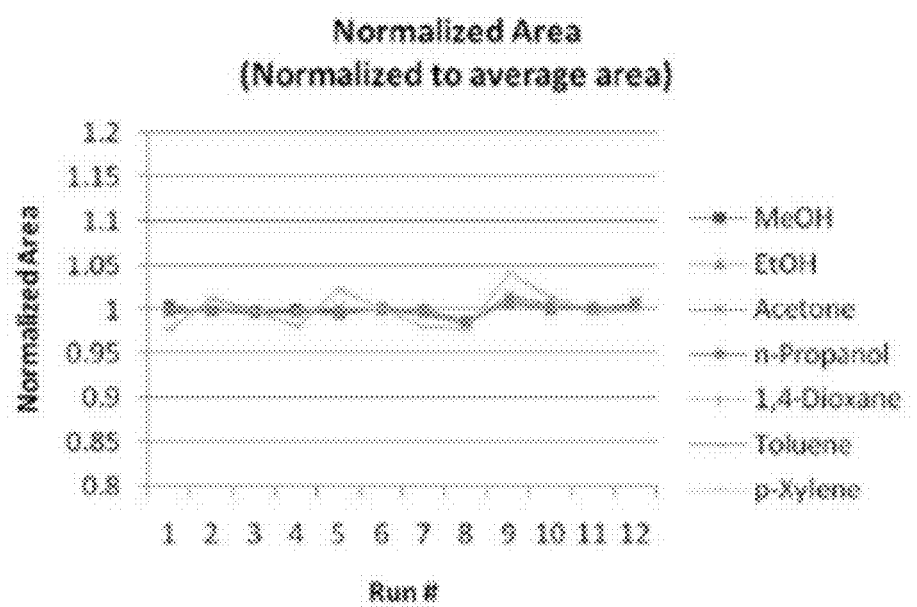

In one experimental example, a head space analysis system as described herein was used to analyze a head space having the following components: methanol (MeOH), ethanol (EtOH), acetone, n-propanol, 1,4-dioxane, toluene, and p-xylene. In this example, the head space was analyzed in twelve different gas sample runs. During each run, the gas sample was transferred from the head space to the sample loop during venting of the head space at a predetermined rate, as described herein. After the sample loop received the gas sample, the gas sample was subsequently transferred from the sample loop to a head space analyzer following stabilization of the pressure within the head space, as described herein. FIG. 5 includes a graph depicting the normalized areas of the different head space components over the course of the twelve sample runs. This graph indicates that the areas of the different head space components had only minimal fluctuation over the course of the twelve samples. FIG. 5 also includes a table with row "area" indicating the relative standard deviation of the areas corresponding to each head space component. The relative standard deviation of the measured area of each head space component corresponds to the area repeatability of the head space analysis system for that particular head space component. Therefore, the head space analysis system of this example consistently demonstrated an area repeatability of about 1% for the various head space components.

Figures 6A, 6B:
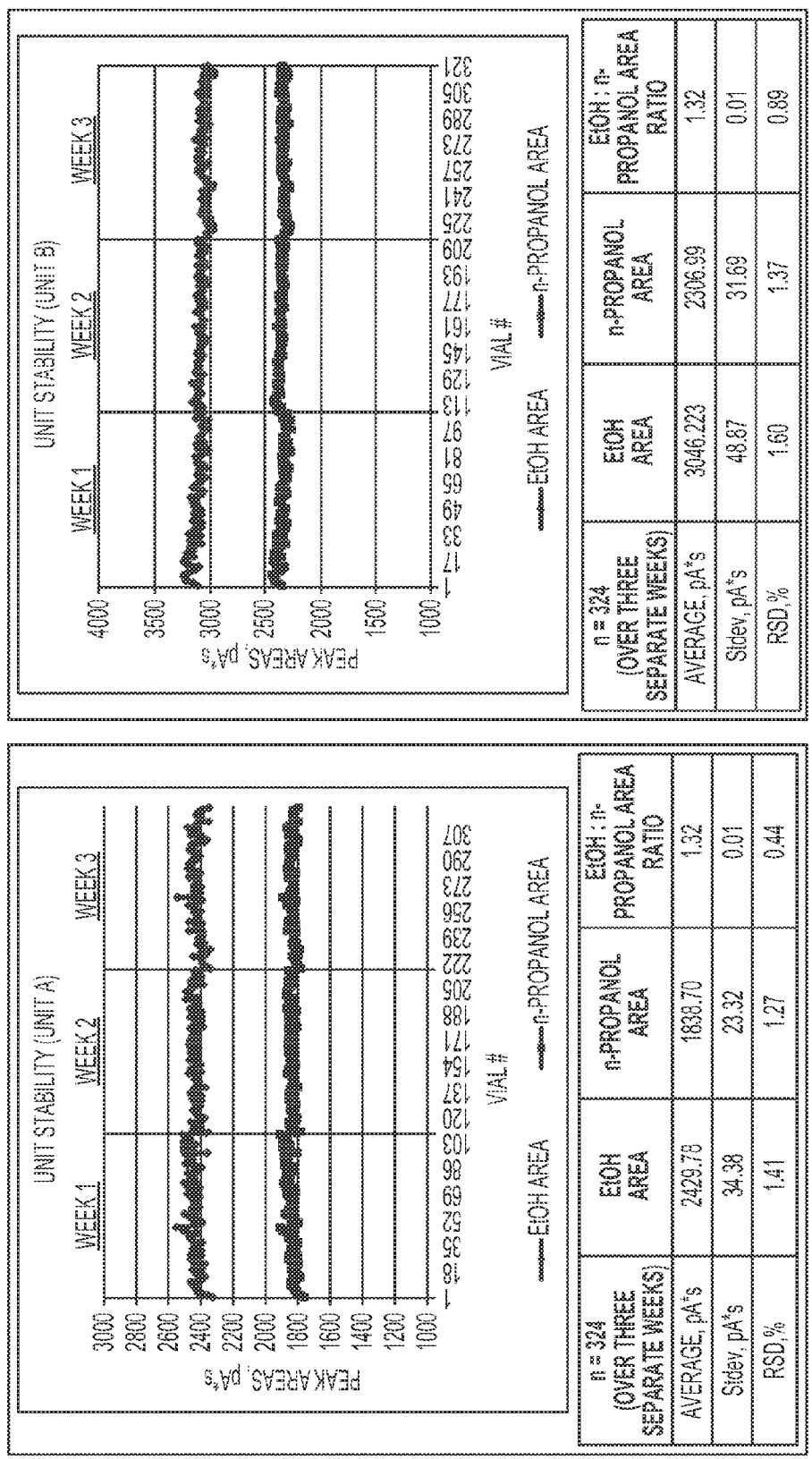

In another experimental example, a first head space analysis system as described herein (Unit A) was used to analyze a first series of head space samples containing ethanol and n-propanol, and a second head space analysis system as described herein (Unit B) was used to analyze a second series of head space samples containing ethanol and n-propanol. Each series of head space samples consisted of 324 different head space samples that were analyzed over the course of three weeks. During each analysis run, a portion of the head space was transferred from the head space to the sample loop during venting of the head space at a predetermined rate, as described herein. After the sample loop received a portion of the head space, the head space sample was subsequently transferred from the sample loop to a head space analyzer following stabilization of the pressure within the head space, as described herein. FIG. 6A demonstrates the unit stability of Unit A, while FIG. 6B demonstrates the unit stability of Unit B. The graphs in FIGS. 6A and 6B illustrate the consistency of the peak areas associated with each head space component over the course of analysis of 324 separate head space samples. The tables in FIGS. 6A and 6B illustrate the average peak areas associated with each head space component, the standard deviations associated with the average peak areas of each head space component, and the relative standard deviations associated with the peak areas of each head space component, as measured relative to all 324 head space samples. FIG. 6A indicates that the area repeatability of Unit A was about 1.41% for ethanol and 1.27% for n-propanol. FIG. 6B indicates that the area repeatability of Unit B was about 1.60% for ethanol and 1.37% for n-propanol. Thus, both Unit A and Unit B provided comparable stability in the areas associated with the components of the sequential head space samples.

In an additional experimental example, the area sensitivity of a head space analysis system (an "active" system) as described herein was compared to the area sensitivity of a conventional head space analysis system (a "passive" system). Both the passive system and the active system were used to pressurize a vial containing a head space to a gauge pressure of 15.00 psi (psig). The passive system was used to vent the head space at an uncontrolled rate, leading to a sudden drop in pressure (shown as a ramp rate of 999 psig/min. in FIG. 7) and a gauge pressure within the vial of 0 psig. In contrast, the active system was used to vent the head space at a predetermined rate of 20.00 psig/min. as described herein. This controlled drop in pressure continued until a predetermined pressure setpoint of 10 psig was reached within the vial. During the venting of each head space, portions of each head space entered into a sample loop of each respective system. The table in FIG. 7 shows that, for each head space component, the passive system produced significantly smaller average areas than the active system.

Figure 8A:
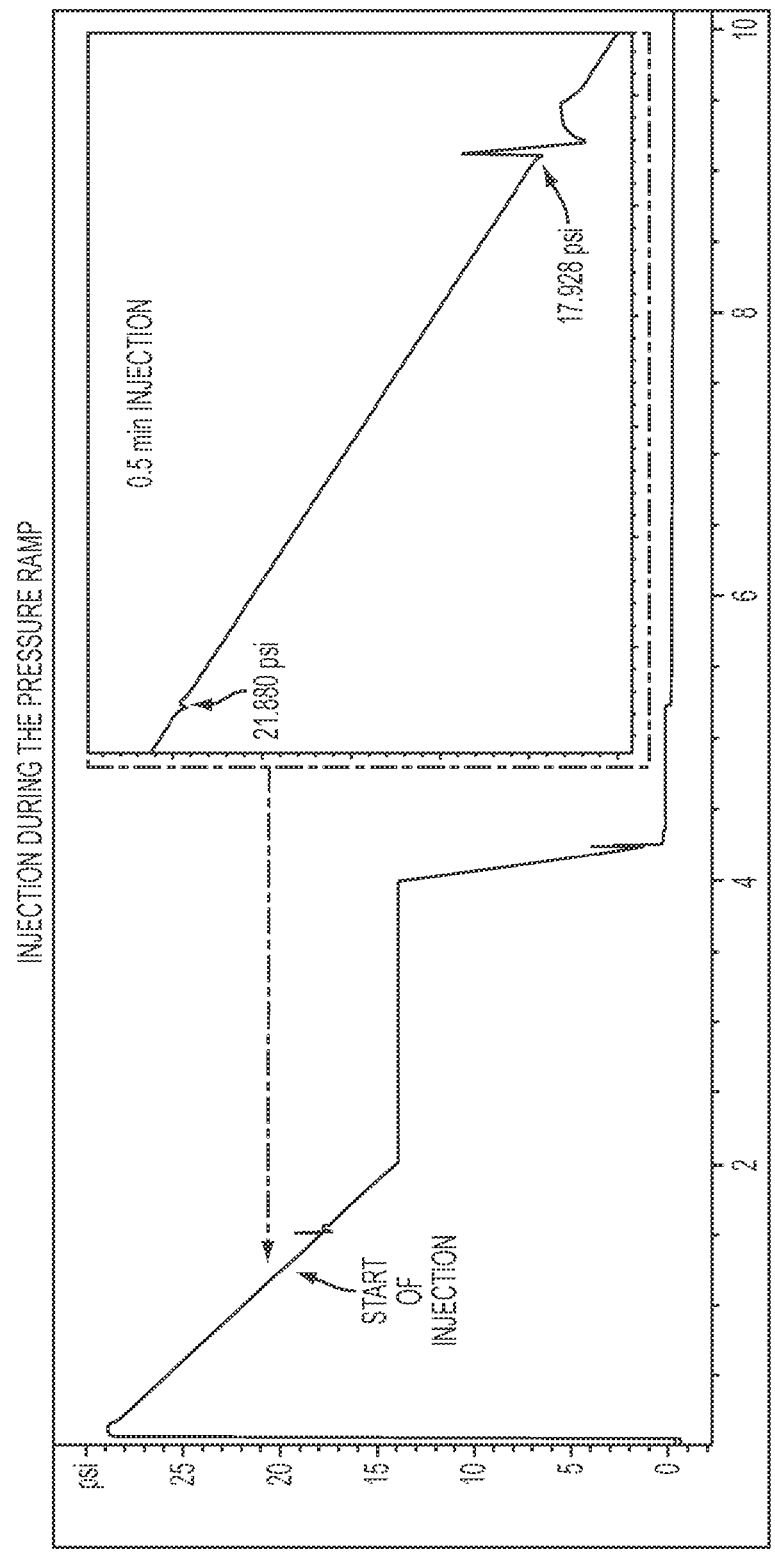
Figure 8B:
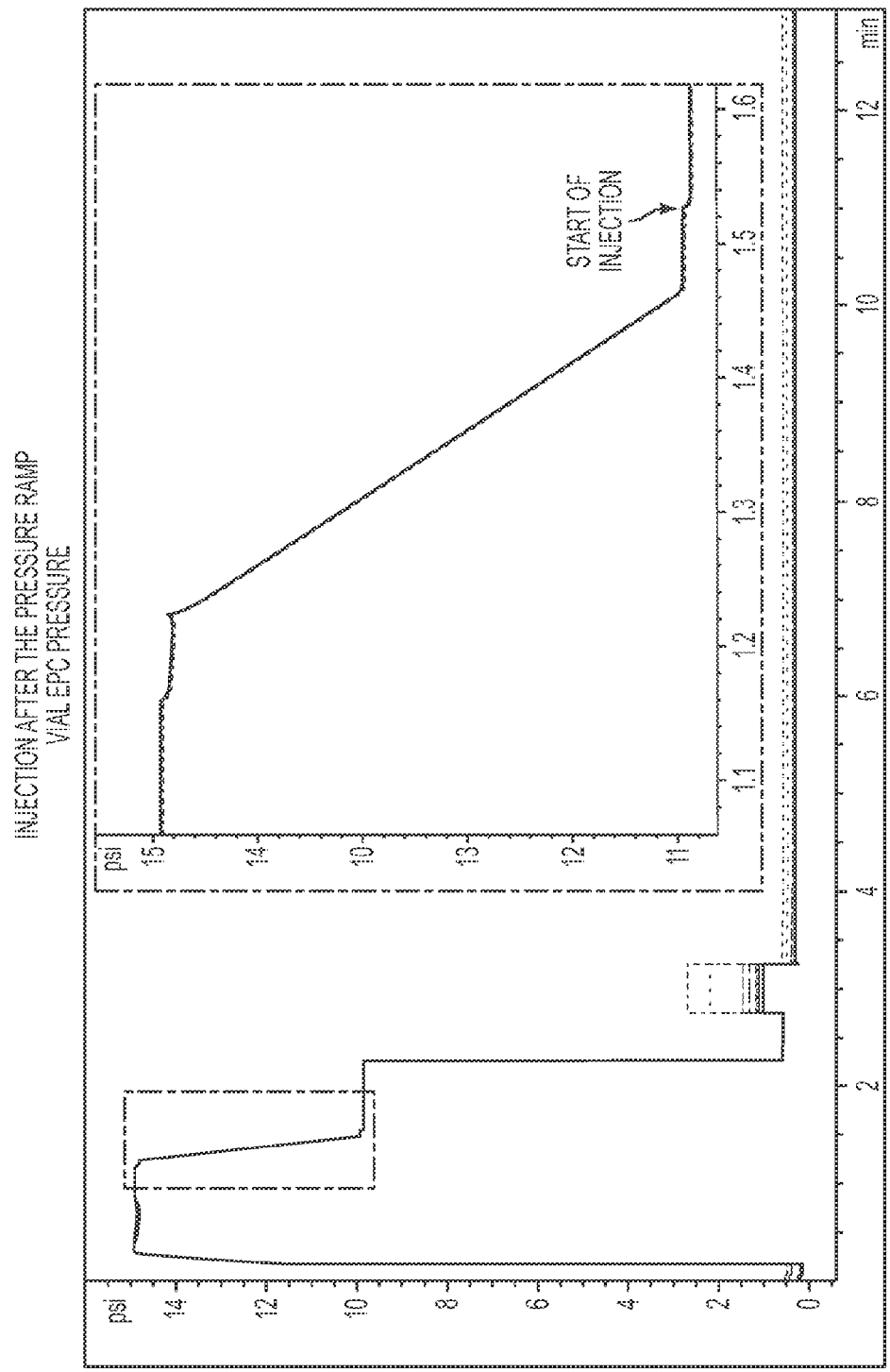

In a further experimental example, a head space sampling system as described herein was used to evaluate conditions under which a head space sample within a sample loop can be transferred to a head space analyzer, as described herein. FIGS. 8A and 8B both demonstrate the gauge pressure within the vial containing the head space as the head space is vented at a predetermined, substantially linear rate to thereby transfer a portion of the head space into the sample loop (a head space sample), as described herein. FIG. 8A graphically displays the change in gauge pressure that occurs within the vial upon transfer of a head space sample to a head space analyzer during venting of the head space. FIG. 8B graphically displays the change in gauge pressure that occurs within the vial upon transfer of a head space sample to a head space analyzer following stabilization of the pressure within the vial, as described herein.

EXEMPLARY EMBODIMENTS

Exemplary embodiments of the present invention include, but are not limited to, the following:
1. A method for sampling a head space of a vial, comprising:
    pressurizing the vial with a pressurization gas from a pressurization gas source;
    establishing fluid communication between the vial and a sample loop;
    establishing fluid communication between the sample loop and a ventilation pathway;
    venting the vial at a predetermined rate to the ventilation pathway via the sample loop, thereby enhancing gas flow from the head space to the sample loop.
2. The method of embodiment 1, further comprising heating the vial.
3. The method of embodiment 1 or 2, wherein the predetermined rate ranges from above 0 to about 25 kPa/sec.
4. The method of embodiment 1 or 2, wherein the predetermined rate is about 2.3 kPa/sec.
5. The method of any one of embodiments 1-3, wherein said venting results in an exponential pressure drop in the vial.
6. The method of any one of embodiments 1-3, wherein said venting results in a linear pressure drop in the vial.
7. The method of any one of the preceding embodiments, further comprising monitoring the gas pressure within the head space, and stopping the venting when the gas pressure within the head space decreases to a predetermined pressure setpoint.
8. The method of embodiment 7, wherein said predetermined pressure setpoint ranges from about 100 to about 800 kPa.
9. The method of embodiment 7, wherein said predetermined pressure setpoint is about 170 kPa.
10. The method of any one of the preceding embodiments, wherein the ventilation pathway comprises a valve which can be adjusted to control the rate of venting.
11. The method of any one of the preceding embodiments, wherein the sample loop is connectable with both the pressurization gas source and the ventilation pathway, and the pressurization gas is applied to the vial via the sample loop.
12. The method of any one of the preceding embodiments, further comprising establishing fluid communication between the sample loop and a head space analyzer to allow gas flow from the head space to the head space analyzer through the sample loop.
13. The method of embodiment 12, further comprising establishing fluid communication between the sample loop and a carrier gas source to cause a carrier gas to flow from the carrier gas source to the sample loop, such that at least a portion of the gas in the sample loop is forced into the head space analyzer.
14. The method of embodiment 12 or 13, further comprising stopping venting before establishing fluid communication between the sample loop and the head space analyzer.
15. A head space sampling device, comprising:
    a sample loop connectable in fluid communication with a vial for providing a head space;
    a pressurization conduit for supplying a pressurization gas to the vial;
    a ventilation pathway connectable in fluid communication with the sample loop, the ventilation pathway having an outlet for venting; and
    a controller in communication with and adapted to adjust said ventilation pathway to vent from the vial to the ventilation pathway at a predetermined rate.
16. The head space sampling device of embodiment 15, wherein the pressurization conduit is connected to the sample loop.
17. The head space sampling device of embodiment 15 or 16, further comprising a heater for heating the vial.
18. The head space sampling device of any one of embodiments 15-17, wherein the controller comprises a computer-readable storage medium comprising instructions for conducting the method of any one of embodiments 1-14.
19. A head space analysis system comprising the head space sampling device of any one of embodiments 15-18, and a head space analyzer.
20. A computer-readable storage medium comprising instructions for conducting the method of any one of embodiments 1-14.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed hereinabove, and that many modifications and other embodiments are intended to be included within the scope of the appended claims. Moreover, although specific terms are employed herein, as well as in the claims which follow, they are used only in a generic and descriptive sense, and not for the purposes of limiting the described invention, nor the claims which follow.

What is claimed is:

1. A method for controlling a rate of gas depressurization within a vial having a head space to be sampled by a head space sampling device, said head space sampling device having a ventilation pathway connectable in fluid communication with a lower pressure environment, and a sample loop connectable between and in fluid communication with said head space and said ventilation pathway, said method comprising:
    establishing fluid communication between said sample loop and said head space,
    establishing a sample gas pressure within said head space, said sample gas pressure being greater than the pressure in said lower pressure environment;
    connecting said sample loop in fluid communication with said lower pressure environment through said ventilation pathway; and venting gas from said head space through said sample loop to said lower pressure environment, thereby allowing sample gas to flow from said head space to said sample loop, to provide a predetermined rate of gas depressurization within the head space and sample loop, wherein the pressure of sample gas in said head space and sample loop is directly controlled by said predetermined rate of gas depressurization to a predetermined head space pressure setpoint less than the initial sample gas pressure.

2. The method according, to claim 1, further comprising: heating said vial to produce a vapor in said head space containing said gas sample.

3. The method according to claim 1, wherein said head space sampling device further comprises a pressurization gas conduit having an inlet for receiving a pressurization gas, said pressurization gas conduit being connectable in fluid communication with said head space of said vial, and wherein establishing the sample gas pressure within said head space comprises:

establishing fluid communication between said head space and said pressurization gas conduit; and pressurizing said pressurization gas conduit with said pressurization gas.

4. The method according to claim 1, wherein said vial comprises a septum, and wherein establishing fluid communication between said sample loop and said head space comprises penetrating said septum with a needle having a bore that is in fluid communication with the sample loop.

5. The method according to claim 1, wherein said predetermined rate of depressurization of said head space to said lower pressure environment ranges from above 0 kPa/sec. to about 25 kPa/sec.

6. The method according to claim 1, wherein said predetermined rate of depressurization of said head space to said lower pressure environment is about 2.3 kPa/sec.

7. The method according to claim 1, wherein said head space sampling device is connectable to a head space analyzer and a carrier gas conduit with an inlet for receiving a carrier gas, and wherein said sample loop is connectable to allow fluid communication either between said head space and said ventilation pathway or between said carrier gas conduit and said head space analyzer, said method further comprising:

establishing fluid communication between said carrier gas conduit, said sample loop, and said head space analyzer; and pressurizing said carrier gas conduit with said carrier gas such that at least portion of said sample gas within said sample loop is forced into said head space analyzer.

8. The method according to claim 7, wherein establishing fluid communication between said carrier gas conduit, sample loop, and said head space analyzer occurs during venting of gas from said head space through said sample loop to said lower pressure environment at said predetermined rate of depressurization.

9. The method according to claim 7, farther comprising: monitoring the gas pressure within said head space; and allowing, said gas pressure within said head space to substantially stabilize prior to establishing fluid communication between said carrier gas conduit, said sample loop, and said head space analyzer.

10. The method according to claim 1, wherein said predetermined rate of depressurization of said head space to said lower pressure environment corresponds to a substantially exponential decrease of the gas pressure within said head space.

11. A method for controlling a rate of gas depressurization within a vial having a head space to be sampled by a head space sampling device, said head space sampling device having a ventilation pathway connectable in fluid communication with a lower pressure environment, and a sample loop connectable between and in fluid communication with said head space and said ventilation pathway, said method comprising:

establishing fluid communication between said sample loop and said head space;

establishing a sample gas pressure within said head space, said sample gas pressure being greater than the pressure in said lower pressure environment;

connecting said sample loop in fluid communication with said lower pressure environment through said ventilation pathway;

venting gas from said head space through said sample loop to said lower pressure environment, thereby allowing sample gas to flow from said head space to said sample loop, to provide a predetermined rate of gas depressurization within the head space and sample loop; and monitoring the sample gas pressure within said head space, wherein gas is vented from said head space through the sample loop to said lower pressure environment, such that said sample gas pressure within said head space gradually decreases to a predetermined pressure setpoint, wherein the pressure of sample gas in said head space and sample loop is directly controlled by said predetermined rate of gas depressurization and said predetermined pressure setpoint is less than the initial sample gas pressure.

12. The method according to claim 11, wherein said predetermined pressure setpoint ranges from about 100 to about 800 kPa.

13. The method according to claim 11, wherein said predetermined pressure setpoint is about 170 kPa.

14. A method for controlling a rate of gas depressurization within a vial having a head space to be sampled by a head space sampling device, said head space sampling device having a ventilation pathway connectable in fluid communication with a lower pressure environment, and a sample loop connectable between and in fluid communication with said head space and said ventilation pathway, said method comprising:

establishing fluid communication between said sample loop and said head space;

establishing a sample gas pressure within said head space, said sample gas pressure being greater than the pressure in said lower pressure environment;

connecting said sample loop in fluid communication with said lower pressure environment through said ventilation pathway; and venting gas from said head space through said sample loop to said lower pressure environment, thereby allowing sample gas to flow from said head space to said sample loop, to provide a predetermined rate of gas depressurization within the head space and sample loop, wherein the pressure of sample gas in said head space and sample loop is directly controlled by said predetermined rate of gas depressurization to a predetermined head space pressure setpoint less than the initial sample gas pressure,
wherein said predetermined rate of gas depressurization is substantially linear.

* * * * *